Jan. 16, 1940. I. RINGDAHL Plant Pat. 353
ROSE
Filed March 9, 1939
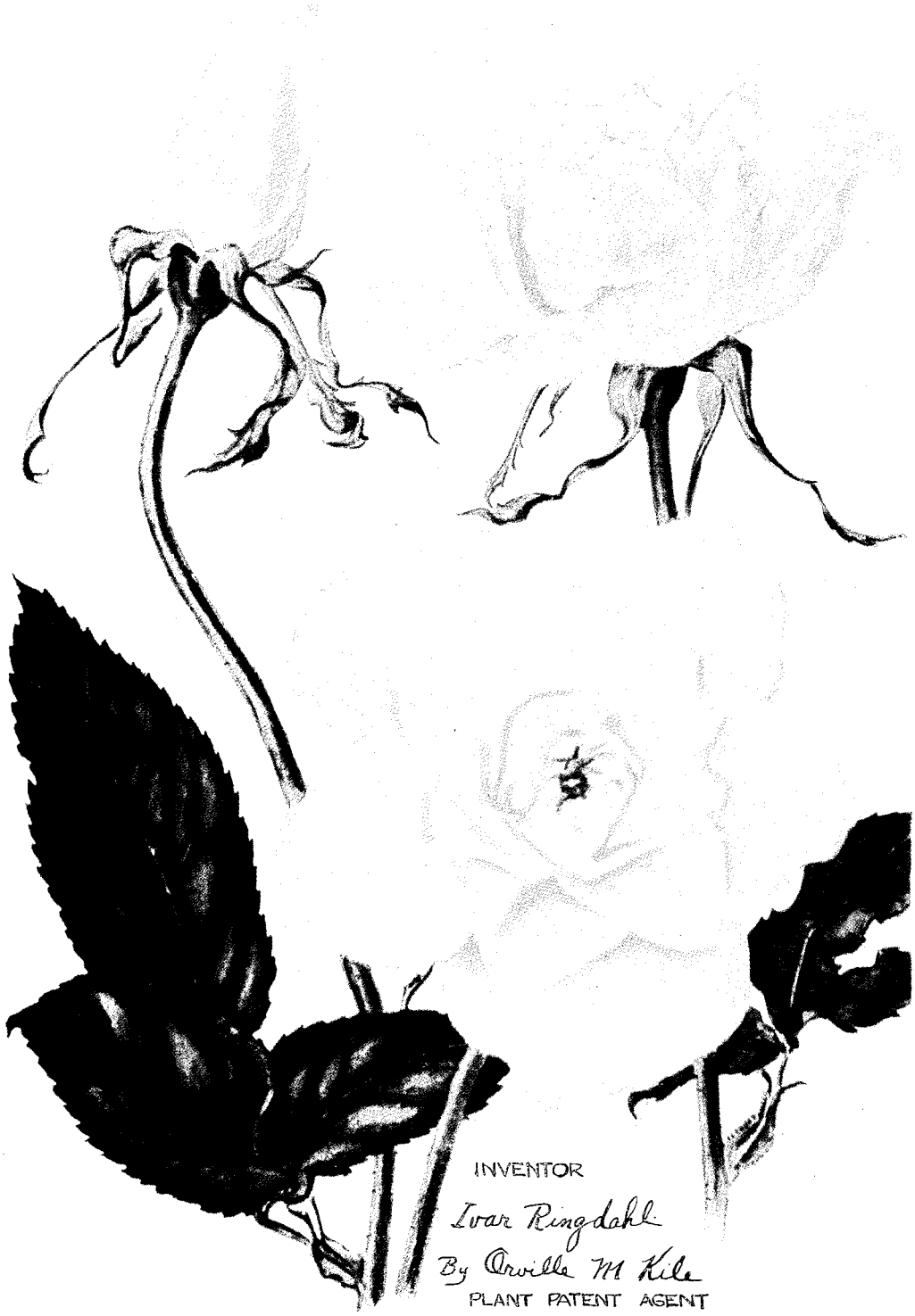

Patented Jan. 16, 1940

UNITED STATES PATENT OFFICE

353

ROSE

Ivar Ringdahl, Rome, N. Y.

Application March 9, 1939, Serial No. 260,869

1 Claim. (Cl. 47—61)

My present discovery relates to a new and distinct variety of hybrid tea rose, particularly to variegations of shades of red and orange on a yellow base. This variety was discovered as a sporting branch of the "Mrs. Franklin D. Roosevelt" and from this branch I have asexualy reproduced stock which has come true to form. It has some of the characteristics of its parent but differs in several respects, particularly in color. Other important differences are: its larger petals of heavier substance; its longer and fuller bud; its darker foliage; its stronger growth and stems; and its more foliaceous sepals.

The original illustrations accompanying this application show in full color and approximately natural size, three specimens of this variety in different stages of opening, as made in the month of February.

Following is a detailed description of this variety of rose. Color plate references indicate Ridgway's Color Standards and Nomenclature. When no plate is indicated, the usual dictionary term is intended.

*The plant*

Growth:

Very vigorous and strong. Upright bush.

*Stems.*—Strong, long and straight. Oil green (Plate V). Peduncle—stiff and unusually long. Covered with numerous long, fine spines. Thorns—quantity and general appearance identical with parent variety.

*Foliage.*—Scarce on upper portion of bush. Leaflets—3 to 5, sometimes 7. Shape—elliptical with acute base. Length about twice width. Size—large. Terminal leaflets about 3½ inches long. Lateral leaflets smaller. Color—dark green—darker than the foliage of its parent. The shade in Ridgway's which most nearly approaches this foliage is Dark Dull Yellow-Green (Plate XXXII). However, the foliage is very glossy. The under side of the leaves is approximately Forest Green (Plate XVII). Substance—leathery. Margin—serrations sharp-pointed.

*Rachis.*—Medium size; smooth; very short between leaflet and stipule.

*Stipules.*—Broad, clinging except for the sharp points.

*Sepals.*—Long and foliaceous; same color as leaves.

Blooming habit:

Flowers borne singly on long stems. Free and continuous bloomer.

*The flower*

Bud:

*Shape.*—Long, and slender.

*Size.*—Large—1½ to 2 inches in length, just before opening.

*Color.*—Light Cadmium (Plate IV) overlaid with shades ranging from Apricot Orange (Plate XIV) through Carnelian Red (Plate XIV), Carrot Red (Plate XIV), Begonia Rose (Plate I), to Eugenia Red (Plate XIII). The amount and nature of the variegation varies in different specimens. Sometimes the variegating color seems laid on in large splotches and in other specimens it has more of the speckled or lined effect, with the yellow showing through. In the most typical specimens the petals are almost completely covered with the red and orange shades except at the base and a narrow strip along the midrib, at which points the Light Cadmium (Plate IV) is seen.

*Opening.*—Opens slowly and evenly.

Blossom:

*Size.*—A fully opened blossom often attains a diameter of five or six inches.

*Form.*—Globular; later cup-shaped with outer petals opening wide. The cup shape is retained until the flower dies.

*Petalage.*—Double, with 25 or 26 petals in the month of December. Petals: Size—outer petals 2 inches wide, slightly longer. Shape—outer petals almost round but length measures slightly more than width. Substance—heavy; leathery. Aspect—surface dull. Color—description of bud applies also to outside surface of outer flower petals. The inner surface of the outer petals is variegated similarly except that the colors are a little less vivid. The inner petals show very little variegation, particularly on their inner surface which is almost a clear Light Cadmium (Plate IV). The effect of the open rose is of an intense yellow rose framed by petals variegated by shades of orange and red. The amount of variegation differs as between specimens.

*Fragrance.*—Has a decided tea fragrance.

*Longevity.*—Keeps exceptionally well after being cut.

*Behavior.*—Petals cling until flower withers.

*Reproductive organs*

Stamens:

Many; arranged about bunched pistils.

*Filaments.*—Irregular lengths, extending higher than pistils; yellow.

*Anthers.*—Large; dark yellow.

Pistils:

Many; bunched.

*Styles.*—White with pink tint at top; medium length and uneven.

*Stigmas.*—Light yellow.

Ovary:

Large.

Pollen:

Scarce or lacking.

Having thus disclosed my discovery, I claim;

A new and distinct variety of hybrid tea rose plant substantially as shown and described, characterized particularly by its very dark foliage with unusually long terminal leaflets; its strong and vigorous growth; its long, strong stems and peduncles; its long, slender bud; and its large flowers with decided tea fragrance and petals of large size, heavy substance and distinctive variegated color composed of shades from Apricot Orange to Eugenia Red overlaid upon Light Cadmium.

IVAR RINGDAHL.